Figure 1:
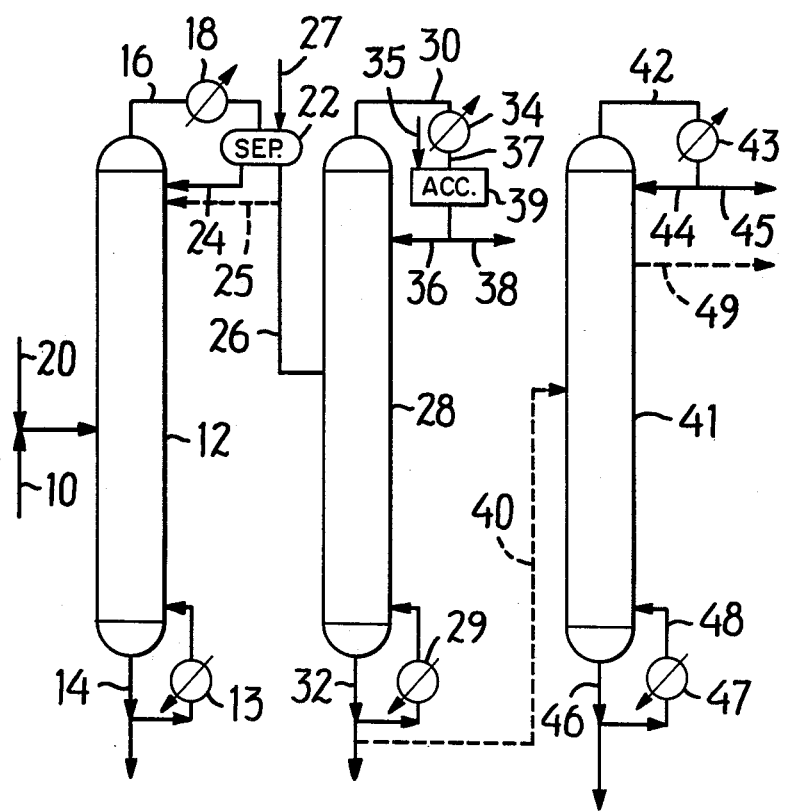

United States Patent [19]

Becker et al.

[11] 4,151,048

[45] Apr. 24, 1979

[54] RECOVERY OF ALKYLENE GLYCOLS BY AZEOTROPIC DISTILLATION

[75] Inventors: Mitchell Becker, Teaneck, N.J.; Howard M. Sachs, Riverdale, N.Y.

[73] Assignee: Halcon Research and Development Corporation, New York, N.Y.

[21] Appl. No.: 804,033

[22] Filed: Jun. 6, 1977

[51] Int. Cl.$^2$ .................. B01D 3/36; C07C 29/28
[52] U.S. Cl. .......................... 203/6; 203/49; 203/69; 203/81; 568/868
[58] Field of Search .............. 203/69, 4, 49, 74, 75, 203/81, 82, 84, 6–9; 260/348.37, 637 R; 568/868

[56] References Cited

U.S. PATENT DOCUMENTS

| | | | |
|---|---|---|---|
| 2,619,452 | 11/1952 | Jones et al. | 203/4 |
| 3,154,583 | 10/1964 | Dombrow et al. | 203/6 |
| 3,809,724 | 5/1974 | Golden | 203/69 |
| 3,864,216 | 2/1975 | Worrell et al. | 203/49 |
| 3,951,756 | 4/1976 | Dirks et al. | 203/4 |
| 4,021,311 | 5/1977 | Becker | 203/69 |
| 4,028,195 | 6/1977 | Becker et al. | 203/95 |
| 4,045,294 | 8/1977 | Becker et al. | 203/69 |

Primary Examiner—Wilbur L. Bascomb, Jr.
Attorney, Agent, or Firm—William C. Long; David Dick; Riggs T. Stewart

[57] ABSTRACT

Ethylene glycol or 1,2-propylene glycol contained in mixtures with lower carboxylate esters of glycol, e.g. as produced by hydrolysis of the esters, is recovered by distillation of the mixtures with a hydrocarbon forming a minimum boiling azeotrope with the ethylene glycol or 1,2-propylene glycol, the hydrocarbon being maintained in an inert atmosphere in the system.

4 Claims, 2 Drawing Figures

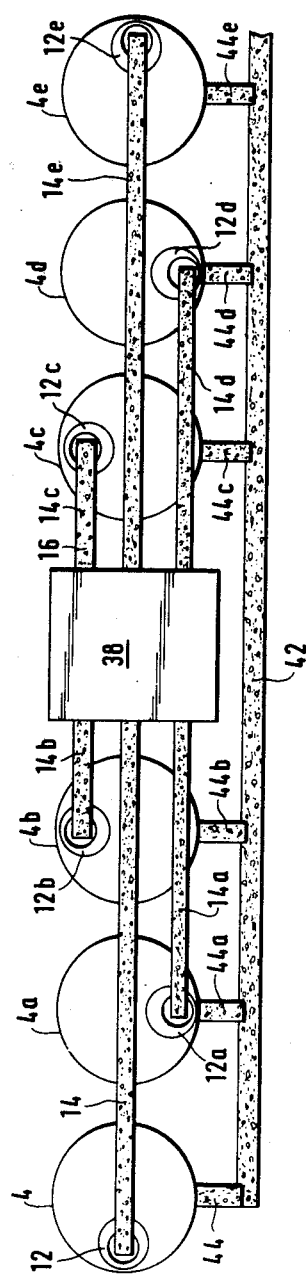

RECOVERY OF ALKYLENE GLYCOLS BY AZEOTROPIC DISTILLATION

This invention relates to the recovery of ethylene glycol or 1,2 propylene glycol from mixtures containing the glycol in admixture with lower carboxylate esters of the glycol, i.e., the ethylene or propylene glycol monocarboxylate and/or the ethylene or propylene glycol dicarboxylate. The invention is more particularly concerned with the recovery of the glycol from mixtures produced by the hydrolysis of lower carboxylate esters of the glycol.

Ethylene glycol and 1,2-propylene glycol (hereafter referred to as propylene glycol) are chemicals of acknowledged commercial importance. Ethylene glycol is used, for example, in the preparation of anti-freeze compositions and in the manufacture of polyester fibers. Ethylene glycol manufacturing processes of commercial interest have generally been based upon ethylene oxide as a raw material. Recently, however, processes have been developed which make it possible to produce ethylene glycol and propylene glycol without the necessity for the intermediate manufacture of the oxide. These processes employ the liquid phase reaction of the olefin, a carboxylic acid and molecular oxygen in the presence of a catalyst to produce carboxylic acid esters of ethylene or propylene glycol. A process of this type is disclosed in U.S. Pat. No. 3,689,535. The glycol can be liberated by hydrolysis of the carboxylate esters produced in these processes. However, the recovery and separation of the glycol produced in the hydrolysis reaction from the unconverted carboxylate esters involves many difficulties because of the formation of glycol-carboxylate ester azeotropes. Golden, U.S. Pat. No. 3,809,724 of May 7, 1974, discloses the recovery of glycols from such mixtures with the carboxylate esters of the glycols by azeotropic distillation. Among the azeotroping agents disclosed are alkyl-substituted aromatic hydrocarbons, particularly methyl-substituted hydrocarbons. While these azeotroping agents are highly effective for the disclosed purpose, when the separated glycol, particularly ethylene glycol, is to be used for some purposes, for example in the manufacture of certain fiber-grade polyesters, it must meet stringent specifications with respect to purity. It was discovered that when hydrocarbons of the character indicated were used as azeotroping agents, the glycol eventually recovered was of a high quality, but it was found to contain, in some cases, small amounts of aromatic oxygenated derivatives, principally alcohols, of the alkyl-substituted aromatic hydrocarbon employed as azeotroping agent, even when the feed to the azeotropic distillation was essentially free of such derivatives, especially under prolonged continuous distillation conditions. While the quantity of such derivatives was small, it nevertheless tended, in some cases, to exceed the limit sometimes desired for fiber-grade glycol, which ordinarily corresponds to an amount of the order of 2 ppm maximum. The content of derivatives can be reduced to acceptable limits by further distillation operations, but this involves some difficulty, particularly in the case of alcohols, and complicates the recovery process. In the following, these aromatic oxygenated derivatives will be referred to simply as alcohols and the quantities of the derivatives will be calculated as the alcohols.

It is accordingly an object of this invention to provide a process for the effective recovery by azeotropic distillation of ethylene glycol or propylene glycol from mixtures of the glycol with lower carboxylate esters of the glycol in a form which is essentially free from alcohols.

Other objects of the invention will be apparent from the following description of the invention and of illustrative embodiments thereof.

It has been surprisingly discovered that the presence of alcohols during azeotropic distillation of glycols in admixture with their carboxylate esters when alkyl-substituted aromatics are used as azeotroping agents can be effectively supressed by employing an azeotroping agent having a limited content of such alcohols and maintaining the azeotroping agent in an inert atmosphere prior to and after its introduction into the azeotropic distillation column. Any inert gas may be employed to provide an inert atmosphere, such as nitrogen, carbon dioxide, argon, helium and the like.

A fuller understanding of the invention will be facilitated by describing the azeotropic distillation system to which the invention is applied, reference being generally made to the above-mentioned Golden U.S. Pat. No. 3,809,724, the disclosure of which is incorporated herein by reference.

While the following description makes particular reference to ethylene glycol, it will be understood that the description is equally and fully applicable to propylene glycol.

Ethylene glycol is separated from mixtures thereof with lower carboxylate esters of ethylene glycol, such as those produced by the hydrolysis of lower carboxylate esters of ethylene glycol, by distilling such mixtures in the presence of an azeotroping agent which is an alkyl-substituted aromatic hydrocarbon, especially a methyl-substituted aromatic hydrocarbon, and which is essentially water-immiscible and forms a minimum-boiling azeotrope with ethylene glycol or propylene glycol and which preferably has a boiling point at atmospheric pressure of 135° to 220° C. When an ethylene glycol-containing mixture is distilled in the presence of such azeotroping agents, the tendency of ethylene glycol to form azeotropes with the mono- and di-ethylene glycol carboxylates is no longer a hindrance to the separation of ethylene glycol from the mixture and the azeotrope with the added azeotroping agent can be readily removed by distillation from the mixture, and the ethylene glycol can be easily recovered from it. The azeotrope, when condensed, separates into two phases, viz. a phase composed essentially of the azeotroping atent and a phase containing the ethylene glycol. The phase containing the azeotroping agent is readily separated, as by decantation, from the ethylene glycol-containing phase and is returned to the distillation column as reflux. Consequently, the azeotroping agent is merely recirculated in the distillation system and the originally-supplied quantity of azeotroping agent is continually available for reuse except for the very small normally-encountered handling losses which are compensated for by make-up azeotroping agent.

Most suitably the alkyl-substituted aromatic hydrocarbon azeotroping agent has an atmospheric boiling point within the 135°–200° C. range at atmospheric pressure. Table A below identifies examples of azeotroping agents of the character indicated and lists the boiling point of the azeotrope with ethylene glycol.

TABLE A

| Azeotroping Agent | Azeotrope b.p., °C. 760 mm. Hg | Agent b.p., °C. 760 mm. Hg |
|---|---|---|
| Ethylbenzene | 133 | 136.2 |
| Cumene | 147 | 152.8 |
| Propylbenzene | 152 | 159 |
| Mesitylene | 156 | 164.6 |
| Pseudocumene | 158 | 169.5 |
| Hemimellitene | 163 | 176.1 |
| p-Cymene | 163.2 | 177 |
| Durene | 174 | 194 |
| Isodurene | 175 | 197 |

As indicated above, the separation process of the invention is applicable to the recovery of ethylene glycol from mixtures of this compound with ethylene glycol lower carboxylate esters produced in any manner, but it is of particular utility in the separation of ethylene glycol from such mixtures produced by the hydrolysis of mono- and/or di-carboxylate esters of ethylene glycol and the separation process can be readily integrated with the hydrolysis operation. The ethylene glycol-ester-feed which is fed to the azeotropic distillation operation of this invention is a mixture of ethylene glycol with lower carboxylate monoesters and/or diesters of ethylene glycol, i.e. esters of ethylene glycol and an alkanoic acid having from 1 to 6 carbon atoms per molecule, such as formic acid, acetic acid, propionic acid, butyric acid, isobutyric acid, and the valeric and caproic acids. Accordingly, the lower carboxylate monoesters of ethylene glycol include ethylene glycol monoformate, ethylene glycol monoacetate, ethylene glycol monopropionate, ethylene glycol monobutyrate, ethylene glycol monoisobutyrate, the ethylene glycol monovalerates and the ethylene glycol monocaproates, and the diesters include the corresponding diesters of the same alkanoic acids. Ethylene glycol admixed with the ethylene glycol monoformate, ethylene glycol monoacetate, monopropionate, monobutyrate and monoisobutyrate, the corresponding diesters, and mixtures of such monoesters and such diesters, are typical feedstocks and the diacetate-monoacetate mixtures are particularly typical feedstocks. Of course, the ethylene glycol to be separated can also be present in mixtures of esters such as mixtures of ethylene glycol monoacetate and ethylene glycol monopropionate, as well as mixtures with one or more diesters, including mixed diesters such as ethylene glycol acetate propionate. The ethylene glycol-ester mixtures can contain 5 to 95 mol percent of ethylene glycol.

The distillation unit in which the azeotropic distillation is carried out can be any convenient fractional distillation unit, e.g. a plate column or a packed column, having a sufficient number of theoretical plates for the desired separation, generally from 20 to 40 theoretical plates. The temperature will, of course, vary with the particular azeotroping agent, since each agent forms a minimum-boiling binary azeotrope with ethylene glycol having a different boiling point but, in general, pot temperatures of 170° to 240° C. are employed in the distillation. Similarly, pressures of from 400 mm. Hg to 50 psig are suitably employed. The azeotrope, when condensed, separates into a first phase, generally the upper phase, composed primarily of the azeotroping agent and into a second phase, generally the lower phase, composed primarily of ethylene glycol. This ethylene glycol phase may contain a small amount of ethylene glycol monocarboxylate ester which, when present in the system, will tend to distil when the azeotropic mixture to a greater or lesser extent depending on the azeotroping agent employed. The vapor condensate from the azeotropic distillation operation is therefore passed to a separator or decanter and the azeotroping agent-containing phase is returned as reflux to the distillation column. It will be understood, however, that operation outside the above-mentioned temperature and pressure ranges is possible and, the specific choice of specific combinations of conditions is entirely within the scope of persons skilled in the art. Preferably as disclosed in the application of Chun Fei Chueh, Ser. No. 612,825 filed Sept. 12, 1975, the disclosure of which application is incorporated herein by reference, a controlled quantity of the glycol-containing phase is also returned to the distillation column as reflux. The minimum reflux ratio of the glycol-containing phase is typically 0.3:1, preferably 0.5:1, and most preferably 1:1. From a practical standpoint the reflux ratio of the glycol-containing phase is generally not above 8:1 although it can be higher if desired. Preferably, all of the phase containing the azeotroping agent is returned to the distillation column as reflux. When both the azeotroping agent and the product glycol are refluxed to the distillation zone in this manner there is a significant improvement in the purity of the glycol removed as distillate with respect to glycol esters.

Ethylene glycol is recovered from the ethylene glycol phase by distillation, extraction, or other appropriate means, although distillation is preferred. Suitably, the ethylene-glycol-containing phase from the azeotropic condensate is subjected to further distillation to remove an overhead comprising any ethylene glycol monocarboxylate ester which may be present along with a relatively small amount of ethylene glycol, together with any azeotroping agent which may be present. This distillation is carried out under appropriate distillation conditions, most suitably at temperatures of 150° to 210° C., and pressures of 150 mm. Hg to 5 psig. The overhead product from this last-mentioned distillation can be recycled to the hydrolysis step when the azeotropic distillation is integrated with the hydrolysis of glycol esters, as described below. Purified ethylene glycol is withdrawn as bottoms product and may be further distilled, if desired.

As mentioned above, the ethylene glycol recovery process described herein is particularly adapted to be integrated with the hydrolysis of ethylene glycol lower carboxylate esters, i.e. ethylene glycol lower carboxylate monoesters, diesters and mixtures of monoesters and diesters, i.e. it can follow the hydrolysis operation in order to recover the ethylene glycol which is produced. Thus, the ethylene glycol-ester feed to the azeotropic distillation can comprise the effluent from the hydrolysis of ethylene glycol carboxylate esters, suitably after removal of water and carboxylic acid, which effluent will contain not only the ethylene glycol monoester and generally the ethylene glycol diester but will also contain varying amounts of ethylene glycol. Thus, the reaction mixture from which the ethylene glycol is to be separated can be prepared by partially hydrolyzing mono-or di-carboxylate esters of ethylene glycol, or mixtures of said esters, by heating the ester or esters in the presence of water. Although the hydrolysis reaction will take place solely under the influence of heat, it may be preferred, in order to increase the rate of reaction, to effect hydrolysis in the presence of an acidic hydrolysis catalyst.

The feed to the hydrolysis operation can consist essentially of the monoester, or of the diester, or of mixtures of mono- or diesters in any proportion. The effluent from reaction which produce ethylene glycol monoester or ethylene glycol diester, or mixtures of the two, can be fed to the hydrolysis reaction. Typical reaction effluents of this nature are described, for example, in the above-mentioned U.S. Pat. No. 3,689,535, wherein the monoester is produced in the presence of substantial quantities of the diester, and in British Pat. No. 1,124,862, wherein the production of monoester substantially free diester is disclosed. The hydrolysis step can be applied to glycol esters produced in any manner, whether by the process of the U.S. patent or the British patent or by various other processes. The hydrolysis reactions, regardless of the exact composition of the feed, continue until an equilibrium mixture comprising diester, monoester, ethylene glycol, carboxylic acid and water is formed. Before feeding the hydrolysis reaction product to the azeotropic distillation, the water and carboxylic acid are preferably removed from the hydrolysis effluent, e.g. by distillation in any convenient manner, these two compounds being readily separated from the ethylene glycol and the lower carboxylate esters. In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it may be preferred, in order to increase the rate of reaction, to effect hydrolysis in the presence of an acidic hydrolysis catalyst such as a mineral acid, e.g. sulphuric acid and phosphoric acid, but most preferably a solid catalyst, e.g. in the form of an acidic ion exchange resin, is employed. The hydrolysis step is thus suitably carried out by causing the glycol ester or ester mixture to react under the influence of heat (with or without a catalyst) to liberate (i.e. hydrolyze) from 15 to 80 mol % of the acyl moieties, e.g. acetate moieties, as lower carboxylate acid, e.g. acetic acid. At the same time ethylene glycol is liberated.

In the hydrolysis reaction, it is desirable to use at least 0.25 mol of water per equivalent of acyl moiety present in the hydrolysis feed. Preferably the amount of water added is in the range of from about 0.75 to 5 mols of water per equivalent of acyl moiety. Of course, greater amounts of water can be used, for example up to 20 mols per equivalent of acyl moiety, but the use of such large amounts of water is both unnecessary and economically disadvantageous. Hydrolysis operating conditions and further reference to hydrolysis catalysts and their use will be found in the detailed data contained in the above-mentioned Golden U.S. Pat. No. 3,809,724.

Following the hydrolysis reaction, the hydrolyzate, which contains carboxylic acid, e.g. cetic acid, and water, in addition to ethylene glycol, monoesters, and diesters, is, as mentioned, suitably passed into a distillation column wherein a major portion of the carboxylic acid and water is vaporized and removed as overhead for subsequent recovery. This separation can be carried out in any conventional distillation column, such as used for the azeotropic distillation. In general, it is desirable to separate at least 90% of the water and carboxylic acid present in the mixture before proceeding with the removal and recovery of the ethylene glycol. Although, as mentioned, the distillation step to separate water and carboxylic acid can be carried out over a wide range of conditions, it has been found preferable to operate at pot temperatures of 170° to 240° C. and at pressures of from 400 mm. Hg to 50 psig. It will be understood that the water and carboxylic acid can be removed in a single distillation operation or the distillation may be carried out in two distillation zones in series with the water and some of the carboxylic acid being removed in the first distillation zone and the remainder of the carboxylic acid to be removed being separated in the second distillation zone. The above-described preliminary distillations are suitably carried out in the manner discussed and exemplified in Golden U.S. Pat. No. 3,809,724.

In carrying out the azeotropic distillation operation, and in carrying out the distillation operations described in the preceding paragraph wherein azeotropic agent may be present as a reslt of its presence in the feed to the hydrolysis zone, the azeotroping agent is, when in the liquid phase, at various times pased into separators, accumulators and the like in order to facilitate its movement through the system. In some cases the liquid azeotroping agent is in the presence of other liquid materials, but in most cases it is the predominant component of the body of liquid in the separators and the accumulators. In accordance with the invention, these liquid bodies comprising the azeotroping agent are continuously maintained under an indert gas "blanket" or "pad", i.e. they are continuously present in an inert gas atmosphere. The pressure of the inert gas atmosphere upon the liquid will depend upon the pressure conditions existing in the system. Ordinarily, the inert atmosphere is at the pressure compatible with the system in which it is employed, e.g. it is slightly above the system pressure.

The inert gas atmosphere may be provided in any convenient manner and is readily provided, for example, by connecting the vessel to be "padded" to a source of the inert gas, e.g. a cylinder or tank of the gas under pressure. The source of gas is connected so that a continuous gas atmosphere will exist above the liquid in the vessel.

The invention will be more fully understood by reference to the accompanying drawing, wherein:

FIG. 1 is a diagrammatic view of an ethylene glycol recovery system embodying the azeotropic distillation system of the invention, and FIG. 2 is a similar diagrammatic view of an overall system wherein the azeotropic distillation recovery system is integrated with an ethylene glycol ester hydrolysis.

Referring to the drawing, and more particularly to FIG. 1, an ester feed stream comprising an ethylene glycol ester mixture is fed through line 10 to azeotropic distillation zone 12 which, in the embodiment illustrated, is a distillation column suitably provided with the heating means, e.g. a conventional reboiler 13, and with a bottoms withdrawal line 14 and a overhead vapor line 16, the latter being connected to a condenser 18. If it is desired to add make-up azeotroping agent to the feed, the make-up aent can be introduced through line 20 so that it may be admixed with the ester feed prior to its introduction into the azeotropic distillation zone. The ethylene glycol is removed through line 16 in the form of an azeotrope with the azeotroping agent, and glycol ester is withdrawn through line 14. The overhead vapor from column 12 leaves through line 16 and is condensed in condenser 18, flows to a phase-separator 22, and the condensed azeotroping agent is returned to column 12 through line 24 as reflux, whereas the ethylene glycol phase is withdrawn through line 26 and is introduced into a refining column 28, also provided with a heating means, suitably in the form of a reboiler 29. A portion of the ethylene glycol phase may be refluxed to zone 12 via 25, if desired, as disclosed in the above-mentioned application of Chun Fei Cheuh. In accordance with the invention, the separator 22 is maintained at all times under a blanket of inert gas, i.e. an atmosphere of inert gas is constantly maintained in the separator. The application of the continuous inert atmosphere is indicated by arrow 27. In column 28, ethylene glycol ester and azeotroping agent contained in the ethylene glycol phase withdrawn from phase separator 22 is removed as vapor through line 30, and ethylene glycol in substantially purified form is withdrawn as bottoms through line 32. The vapors in line 30 are condensed in condenser 34 and a portion is returned as reflux to column 28 through line 36 and the remainder is withdrawn through line 38. Some or all of the material in line 38 may be combined with the feed to column 12, and make-p azeotroping agent, as required, is also suitably added as mentioned above through line 20, or added to line 24. In line 37 there is provided an accumulator 39 wherein the condensate is collected prior to passing through line 38. As in the case of separator 22, accumulator 39 is also continuously provided with an atmosphere of inert gas, as indicated diagrammatically by arrow 35. Preferably, the purified ethylene glycol withdrawn through line 32 is given a final distillation to insure against the presence in the product of higher boiling materials such as diethylene glycol and the like, which may tend to form in small amounts. Thus, if this further distillation is desired, the ethylene glycol from line 32 is passed through line 40 into distillation column 41 which is operated at pot or reboiler temperatures of 120° to 190° C. and pressures of 40 mm to 600 mm to remove purified glycol through line 42 leading to condenser 43, the condensate form which is partially returned to column 41 as reflux through line 44, and the remainder is withdrawn through line 45. The heavier components separated by the distillation are removed through line 46. The reboiler 47 in line 48 provides the necessary heat to maintain the distillation. Preferably, the upper few plates, e.g., 2-3 theoretical plates, of column 41 are used as a conventional "pasteurization" section, i.e., the product glycol is removed as a side stream through line 49, and the entire distillate passing into line 42 and condenser 43 is returned as reflux through line 44 except for the withdrawal of a small portion through line 45 containing low-boiling components which may be present.

Referring now to FIG. 2, wherein the azeotropic distillation system just described is integrated with the hydrolysis of lower carboxylate esters of ethylene glycol to provide the feed to azeotropic distillation column 12, a hydrolysis ester feed stream enters a hydrolysis zone 50 through line 52 and line 54 and water for the hydrolywis enters through line 56 and is combined with the hydrolysis ester feed in line 54 before entering zone 50. Zone 50 is suitably filled with a bed of solid hydrolysis catalyst, e.g. a bed of acidic ion exchange resin, and the combined water and ester feed stream flows upwardly through the bed and the hydrolyzed reaction product is removed through line 58. The product stream in line 58 is introduced into a water separator column 60, provided with a reboiler 61 or other heating means. In column 60, water is vaporized and, along with a small amount of carboxylic acid, is withdrawn through line 62 and condensed in condenser 64. Since, in the embodiment illustrated in FIG. 2, the condensate from condenser 64 will contain some azeotroping agent, as will be explained below, the condensate passes to a phase separator 66 wherein the water and carboxylic acid form one phase and the azeotroping agent forms a second phase, the latter being withdrawn from separator 66 through line 68. Separator 66, like separator 22, is continuously maintained in an inert atmosphere, i.e. an atmosphere of an inert gas continuously overlies the liquid in the separator. The inert atmosphere in separator 66 is shown by arrow 69. The aqueous phase is withdrawn through line 70, with part of it being returned to column 60 through line 72 as reflux and the remainder being recycled to reactor 50 through line 74 which empties into water supply 56. The portion of the hydrolysis product stream supplied to column 60 which is not vaporized and withdrawn through line 62 and which comprises ethylene glycol, carboxylic acid and lower carboxylic esters of ethylene glycol is withdrawn through line 75 and fed to a distillation column 76, also provided with appropriate heating means, e.g. a reboiler 77. In distillation column 76, the carboxylic acid is vaporized and carboxylic acid vapors are withdrawn through line 78 and condensed in condenser 80 with some of the condensate being returned to column 76 as reflux through line 82 and the remainder being withdrawn through line 84. The carboxylic acid stream will also contain any water which was not separated in column 60. This carboxylic acid stream is advantageously recycled to the olefin oxidation zone, e.g. of the type described in U.S. Pat. No. 3,689,535, to produce further quantities of glycol esters which provide the feed to the hydrolysis. The carboxylic acid stream is substantially free from any azeotroping agent which is desirable since hydrocarbons of this type have an adverse effect upon the oxidation reaction. The essentially water- and carboxylic acid-free ethylene glycol-lower carboxylate ester mixture is withdrawn from distillation zone 76 through line 86 and is supplied to line 10 to provide the ester feed to azeotropic distillation zone 12, as described above in connection with the discssion of FIG. 1. To complete the integration of the azeotropic distillation system with the hydrolysis system, a line 90 connects with line 38 to conduct the withdrawn condensate containing azeotroping agent from column 28 to the feed to hydrolysis zone 50. A side stream from column 12 comprising vapors of lower carboxylate esters of ethylene glycol is withdrawn through line 92 and also combined with the feed to the hydrolysis zone, after being condensed by the condenser 88. A small purge stream comprising liquid esters is withdrawn through line 14. It is this azeotropic agent in the condensate in line 90, as well as a small amount appearing in the stream in line 92, which is collected in separator 66 and returned to the azeotropic distillation operation via line 68 which communicates with the reflux stream in line 24. It will be understood that in a commercial plant there will generally be additional vessels, e.g. reflux drums, into which the azeotroping agent alone, or in admixture with other liquids, will be passed during its movement through the system. For purposes of simplicity, these supplemental vessels have not been illustrated in the drawing, but it is intended that, when present, they shall be provided with an inert gas "pad" in accordance with the invention.

As previously indicated, the alkyl-substituted aromatic azeotroping agent which is supplied to the system should have a limited content of its oxygenated derivatives, characterized in the foregoing description as alcohols. It has been found that for best results the content of oxygenated derivatives should be at most 100 ppm. If the azeotroping agent to be supplied has greater quantities of such derivatives, it should be distilled. This is done by subjecting the azeotroping agent to simple distillation in an inert atmosphere and recovering it as the overhead condensed distillate. Most advantageously, the azeotroping agent is subjected to reflux in an inert atmosphere, e.g. for one hour or up to several hours, prior to distilling it. The freshly distilled azeotroping agent should then be stored in an inert gas atmosphere prior to use. As previously indicated, the oxygenated derivatives with which the invention is concerned are primarily alcohols and the quantities of oxygenated derivatives mentioned herein are calculated as such alcohols. The alcohols are considered to be aralkyl alcohols, e.g. in the case of trimethyl benzenes, they are dimethyl benzyl alcohols, in the case of tetramethyl benzenes, they are trimethyl benzyl alcohols and are corresponding hydroxy derivatives of other alkyl substituted aromatic hydrocarbons.

The following examples of specific application will serve to give a fuller understanding of the invention but it will be understood that these examples are illustrative only and are not intended as limiting the invention.

EXAMPLE 1

In a system comprising three distillation columns such as shown in FIG. 1, a feed containing 27.5 wt. % of ethylene glycol (EG), 39.7 wt. % ethylene glycol monoacetate (EGMA), 20.7 wt. % ethylene glycol diacetate (EGDA), 9.0 wt. % ethylene glycol monoformate (EGMF), 0.8 wt. % ethylene glycol diformate (EGDF) and 2.3 wt. % ethyelen glycol acetate formate (EGAF) is fed to the azeotrope column 12 at a rate of 2200 g/hr. The azeotrope column consists of 3" diameter, stainless steel column with 35 stripping and 25 rectifying sieve trays. The column is operated at 30 psig and with a bottoms temperature of 234° C. The azeotroping agent used is 1,2,3 tri-methylbenzene (TMB). Prior to its being charged to the system, the TMB is refluxed for 15 hours under nitrogen and then batch distilled in a b 20-tray glass Oldershaw column at a reflux ratio of 2/1. A 10% fore cut and an 80% heart cut are taken. The TMB heart cut contains less than 5 ppm of oxygenated impurities calculated as dimethyl benzyl alcohol (DMBA).

The TMB heart cut is fed to the column on the top tray. Vapors coming overhead from the column and comprising EG, some EG esters, and TMB are condensed in condenser 18 and the condensate flows to a separator 22 where the light TMB-rich phase and the dense EG phase are separated.

The EG phase is decanted to an EG reflux accumulator (not shown) from which a portion is refluxed to the column via line 25 and a portion taken as distillate via line 26, the reflux ratio being 2.2 reflux to one distillate. Distillate composition is 75 wt. % EG, 20 wt. % EGMF, 1.5 wt. % TMB, 1 wt. % EGMA and the remainder various volatile products. The TMB phase is decanted to a TMB reflux accumulator (not shown) in line 24 from which it is refluxed to the column at 5000 ml/hr.

The combined azeotrope column distillate is then fed to the topping column 28 at 960 g/hr. This column is a 2" diameter glass Oldershaw column with 45 stripping and 25 rectifying trays. The column is operated at 220 mm Hg abs. and 170° C. bottoms temperature. The condensate from condenser 34 is fed to accumulator 39 from which reflux is supplied to the column via an automatic reflux splitter, at a reflux ratio of 2/1, and 510 g/h of essentially pure EG are taken as bottoms via line 32. During operation the separator and the accumulators are kept under a nitrogen atmosphere at all times and care is taken to protect the TMB under nitrogen during storage and handling. TMB losses from the system are made up in the TMB reflux accumulator.

These bottoms from column 28 are fed to the product column 41 at 600 g/h. The product column is a 2" diameter glass Oldershaw column with 10 stripping and 25 rectifying trays. It operates at 240 mm HG and 170° C. bottoms temperature. Product EG is taken as a sidestream 49, 5 trays below the top of the column. At a reflux ratio of 0.4/1 (reflux/sidestream) about 96% of the feed is recovered as purified EG. Equal amounts of the overhead distillate and bottoms are recovered via lines 45 and 46, respectively.

The EG sidestream is found to contain 0.2 ppm DMBA.

EXAMPLE 2

Another experiment is conducted under essentially the same column conditions described in Example 1. During this experiment, however, no inert atmosphere is provided and the reflux accumulators are left open to the atmosphere. No precautions are taken to protect the TMB from the atmosphere during storage and handling.

The final EG product contains in excess of 2 ppm DMBA.

EXAMPLE 3

When Example 1 is repeated with an azeotroping agent containing about 100 ppm of oxygenated impurities calculated as DMBA, the product EG obtained contains less than 1 ppm DMBA but when Example 2 is repeated with such an azeotroping agent, the product DMBA contains substantially more than 2 ppm DMBA.

What is claimed is:

1. In the distillation of a mixture comprising ethylene glycol or propylene glycol and the monocarboxylate esters and dicarboxylate esters of the glycol to recover the glycol therefrom, including distillation in the presence of an azeotroping agent which is an alkyl-substituted aromatic hydrocarbon having a boiling point at atmospheric pressure of 135° C. to 220° C., wherein the azeotroping agent is at times in the vapor state and at times in the liquid state and tends to undergo slight chemical reaction while in the distillation system, the improvement which comprises employing an azeotroping agent having a content of oxygenated impurities of at most about 100 ppm and maintaining said azeotroping agent under an atmosphere consisting essentially of an inert gas when said azeotroping agent is in the liquid state at least immediately prior to said distillation and after said distillation while the azeotroping agent is contained in the distillation system.

2. A process as defined in claim 1, wherein during azeotropic distillation an overhead condensed distillate comprising the azeotroping agent is phase separated in a separation zone, said separation zone is maintained under an inert gas atmosphere.

3. A process as defined in claim 1, wherein during distillation an overhead condensed distillate comprising the azeotropic agent is held in an accumulation zone, said accumulation zone is maintained under an inert gas atmosphere.

4. A process as defined in claim 1, wherein the mixture is a hydrolyzate produced by hydrolysis of glycol carboxylate esters to liberate the glycol and the mixture is first distilled to remove water and liberated carboxylic acid, azeotropically distilled and the glycol-containing condensed distillate is then distilled in a second distillation to remove as distillate minor amounts of azeotroping agent and glycol esters from the product glycol, and the last-named distillate is recycled to the hydrolysis step, the azeotroping agent being maintained in the inert gas atmosphere when in the liquid state in the condensed distillates from said azeotropic and said second distillations.

* * * * *